United States Patent
Yang et al.

(10) Patent No.: US 11,452,756 B2
(45) Date of Patent: Sep. 27, 2022

(54) COMPOSITION AND METHOD FOR IMPROVING QUANTITY OF TEAR FLUID, COMPOSITION, TREATING CONSTIPATION AND IMPROVING SKIN QUALITY

(71) Applicant: Tokiwa Phytochemical Co., Ltd., Sakura (JP)

(72) Inventors: Jinwei Yang, Sakura (JP); Tomoko Kuniyoshi, Sakura (JP)

(73) Assignee: TOKIWA PHYTOCHEMICAL CO., LTD., Sakura (JP)

( * ) Notice: Subject to any disclaimer, the term of this patent is extended or adjusted under 35 U.S.C. 154(b) by 0 days.

(21) Appl. No.: 16/854,462

(22) Filed: Apr. 21, 2020

(65) Prior Publication Data

US 2021/0030831 A1 Feb. 4, 2021

Related U.S. Application Data

(63) Continuation-in-part of application No. 16/727,411, filed on Dec. 26, 2019, now abandoned.

(30) Foreign Application Priority Data

Jul. 31, 2019 (JP) ................. 2019-141840

(51) Int. Cl.
| | | |
|---|---|---|
| A23L 33/105 | (2016.01) | |
| A61K 36/906 | (2006.01) | |
| A61K 8/9794 | (2017.01) | |
| A61P 17/00 | (2006.01) | |
| A61P 1/10 | (2006.01) | |
| A61P 27/02 | (2006.01) | |

(52) U.S. Cl.
CPC .......... *A61K 36/906* (2013.01); *A23L 33/105* (2016.08); *A61K 8/9794* (2017.08); *A61P 1/10* (2018.01); *A61P 17/00* (2018.01); *A61P 27/02* (2018.01)

(58) Field of Classification Search
CPC .................................................. A61K 36/00
USPC ........................................................ 424/725
See application file for complete search history.

(56) References Cited

FOREIGN PATENT DOCUMENTS

| | | |
|---|---|---|
| JP | 2009-067731 A | 4/2009 |
| JP | 2013-153397 A | 8/2013 |
| JP | 2013-224326 A | 10/2013 |
| JP | 2015-010078 A | 1/2015 |
| JP | 5756264 B2 | 7/2015 |
| JP | 2016-008180 A | 1/2016 |
| JP | 2017-031120 A | 2/2017 |
| JP | 2017-031121 A | 2/2017 |
| JP | 2017-078032 A | 4/2017 |
| JP | 2018-177654 A | 11/2018 |
| JP | 6417630 B2 | 11/2018 |
| KR | 101406110 B | * 7/2014 |
| KR | 1020150145332 | * 12/2015 |
| WO | 2016/163245 A1 | 10/2016 |

OTHER PUBLICATIONS

Penn Medicine, "Why You Should Cry—5 Reasons to Let It All Out", 2016.*
Antiobesity effects of Kaempferia parviflora in spontaneously obese type II diabetic mice, by Tomoko Akase et al, J Nat Med, vol. 65, pp. 73-80, 2011 (8 pages).
Preventive effect of Kaempferia parviflora ethyl acetate extract and its major components polymethoxyflavonoid on metabolic diseases, by Tsutomu Shimada et al, Fitoterapia, vol. 82, pp. 1272-1278, 2011 (7 pages).
Suppressive effects of methoxyflavonoids isolated from Kaempferia parviflora on inducible nitric oxide synthase (iNOS) expression in RAW 264.7 cells, by Chutha Sae-Wong et al, Journal of Ethnopharmacology, vol. 136 (3), pp. 488-495, 2011 (8 pages).
Potent SIRT1 Enzyme-stimulating and Anti-glycation Activities of Polymethoxyflavonoids from Kaempferia parviflora, by Asami Nakata et al, Natural Product Communications, vol. 9, No. 9, pp. 1291-1294, 2014 (8 pages).
Antiglycative effect of Kaempferia parviflora Wall. Ex. Baker (Zingiberaceae): Prevention of advanced glycation end product formation, by Masayuki Yagi et al, Glycative Stress Research, vol. 5, No. 4, pp. 163-170, 2018 (9 pages).
Biological Characterization of Black Turmeric (*Kaempferia parviflora*) Using an in vitro Assay Panel, by Akihiro Yamaguchi et al, Journal of Nutritional Food, vol. 12, No. 2, pp. 29-35, 2009 (7 pages).
Daily intake of Kaempferia parviflora extract decreases abdominal fat in overweight and preobese subjects: a randomized, double-blind, placebo-controlled clinical study, by Susumu Yoshino et al, Diabetes, Metabolic Syndrome and Obesity, vol. 11, pp. 447-458, 2018 (12 pages).
Effects of Single Oral Intake of Kaempferia parviflora Extract on Energy Metabolism—A Randomized Double-blind Crossover Study—, by Susumu Yoshino et al, Jpn Pharmacol Ther, vol. 44, No. 12, pp. 1757-1762, 2016 (6 pages).
Enhancement of physical fitness by black ginger extract rich in polymethoxyflavones: a double-blind randomized crossover trial, by Kazuya Toda et al, Integr Mol Med, vol. 3, No. 2, pp. 628-634, 2016 (7 pages).
Positive Modulation Effect of 8-Week Consumption of Kaempferia parviflora on Health-Related Physical Fitness and Oxidative Status in Healthy Elderly Volunteers, by Jintanaporn Wattanathorn et al, Evidence-Based Complementary and Alternative Medicine, vol. 2012, Article ID 732816 (7 pages).
Effects of Kaempferia parviflora Extract on Physical Function in Elderly Subjects—A randomized, Double-blind, Placebo-controlled Parallel-group Study—, by Yoshie Yamana et al, Jpn Pharmacol Ther, vol. 47, No. 6, pp. 927-936, 2019 (10 pages).

* cited by examiner

*Primary Examiner* — Michael V Meller
(74) *Attorney, Agent, or Firm* — Flynn Thiel, P.C.

(57) ABSTRACT

The present invention relates to a composition and method for improving the quantity of tear fluid, a composition and method for treating constipation, and a composition and method for improving skin quality. By utilizing an extract of Black ginger (*Kaempferia parviflora*)), the quantity of tear fluid, constipation, and skin quality are improved.

1 Claim, No Drawings

COMPOSITION AND METHOD FOR IMPROVING QUANTITY OF TEAR FLUID, COMPOSITION, TREATING CONSTIPATION AND IMPROVING SKIN QUALITY

CROSS-REFERENCE TO RELATED APPLICATIONS

This application is a continuation-in-part of U.S. application Ser. No. 16/727,411, filed Dec. 26, 2019, which claims the benefit of Japanese Application No. 2019-141840, filed Jul. 31, 2019, hereby incorporated herein by reference.

TECHNICAL FIELD

The present invention is related to a composition and method for improving the quantity of tear fluid, a composition and method for treating constipation, and a composition and method for improving skin quality.

RELATED ART

Black ginger (*Kaempferia parviflora*) is a plant in the genus *Kaempferia* of the plant family Zingiberaceae, which is known as Thai ginseng or Kra chai dahm.

Black ginger is cultivated widely in Thailand, which is the place of origin, and it is taken on a daily basis from old times. It is used for a nourishing tonic, increasing energy, lowering a blood-sugar level, physical recovery, and recovering circulatory organs.

In recent years, many effects of Black ginger (*Kaempferia parviflora*) are reported such as a fat decomposition-promoting action (NON-PATENT DOCUMENT 1, NON-PATENT DOCUMENT 2, PATENT DOCUMENT 1), anti-inflammatory action (NON-PATENT DOCUMENT 3), activation effect for a longevity gene (NON-PATENT DOCUMENT 4, PATENT DOCUMENT 2), anti-saccharification action (NON-PATENT DOCUMENT 4, NON-PATENT DOCUMENT 5), antiallergic action (NON-PATENT DOCUMENT 6), xanthine oxidase inhibition action (PATENT DOCUMENT 3), AMPK activation effect (PATENT DOCUMENT 4), production-inhibiting activity for TNF-☐ and IL-6 (PATENT DOCUMENT 5), energy metabolism promoting action in muscle cells (PATENT DOCUMENT 6), reinforcement effect for muscle amount and endurance of muscle (PATENT DOCUMENT 7, PATENT DOCUMENT 8, PATENT DOCUMENT 9), cerebral function improvement action (PATENT DOCUMENT 10), and improving action for cold-sensitive constitution (PATENT DOCUMENT 11).

Further, in human studies, a reducing effect for abdominal fat and neutral fat in the blood (NON-PATENT DOCUMENT 7), promoting effect for fat combustion in exercise (NON-PATENT DOCUMENT 8), and reinforcement effect for muscle strength and motion function (NON-PATENT DOCUMENT 9, NON-PATENT DOCUMENT 10, NON-PATENT DOCUMENT 11) are confirmed. Human application is expected.

REFERENCES FOR RELATED ART

Non-Patent Document

NON-PATENT DOCUMENT 1 Antiobesity effects of *Kaempferia parviflora* in spontaneously obese type II diabetic mice. J Nat Med, 65, 73-80 (2011).

NON-PATENT DOCUMENT 2 Preventive effect of *Kaempferia parviflora* ethyl acetate extract and its major components polymethoxyflavonoid on metabolic diseases, Fitoterapia, 82, 1272-1278 (2011).

NON-PATENT DOCUMENT 3 Suppressive effects of methoxyflavonoids isolated from *Kaempferia parviflora* on inducible nitric oxide synthase (iNOS) expression in RAW 264.7 cells. Journal of Ethnopharmacology, 136(3), 488-495 (2011).

NON-PATENT DOCUMENT 4 Potent SIRT1 Enzyme-stimulating and Anti-glycation Activities of Polymethoxyflavonoids from *Kaempferia parviflora*, Natural Product Communications, 9(9), 1291-1294 (2014).

NON-PATENT DOCUMENT 5 Antiglycative effect of *Kaempferia parviflora* Wall. Ex. Baker (Zingiberaceae): Prevention of advanced glycation end product formation, Glycative Stress Research, 5 (4): 163-170 (2018).

NON-PATENT DOCUMENT 6 Biological characterization of black turmeric (*Kaempferia parviflora*) using an in vitro assay panel, Journal of Nutritional Food, 12(2), 29-35 (2009).

NON-PATENT DOCUMENT 7 Daily intake of *Kaempferia parviflora* extract decreases abdominal fat in overweight and pre-obese subjects: a randomized, double-blind, placebo-controlled clinical study, Diabetes, Metabolic Syndrome and Obesity,11, 447-458(2018).

NON-PATENT DOCUMENT 8 Effects of single oral intake of *Kaempferia parviflora* extract on energy metabolism—A randomized double-blind crossover study, Jpn Pharmacol Ther, 44(12), 1757-1762 (2016).

NON-PATENT DOCUMENT 9 Enhancement of physical fitness by black ginger extract rich in polymethoxyflavones: a double-blind randomized crossover trial, Integr Mol Med., 3(2), 628-634 (2016).

NON-PATENT DOCUMENT 10 Positive modulation effect of 8-week consumption of *Kaempferia parviflora* on health-related physical fitness and oxidative status in healthy elderly volunteers, Evid Based Complement Alternat Med., Article ID 732816, doi:10.1155/2012/732816 (2012).

NON-PATENT DOCUMENT 11 Effects of *Kaempferia parviflora* extract on physical function in elderly subjects—A randomized, double-blind, placebo-controlled parallel-group study-, Jpn Pharmacol Ther, 47(6), 927-36 (2019).

Patent Documents

PATENT DOCUMENT 1 Japanese Patent Application Publication No. 2013-224326
PATENT DOCUMENT 2 Japanese Patent No. 6417630
PATENT DOCUMENT 3 Japanese Patent No. 5756264
PATENT DOCUMENT 4 Japanese Patent Application Publication No. 2017-31121
PATENT DOCUMENT 5 Japanese Patent Application Publication No. 2017-031120
PATENT DOCUMENT 6 WO2016/163245
PATENT DOCUMENT 7 Japanese Patent Application Publication No. 2017-078032
PATENT DOCUMENT 8 Japanese Patent Application Publication No. 2015-10078
PATENT DOCUMENT 9 Japanese Patent Application Publication No. 2016-008180
PATENT DOCUMENT 10 Japanese Patent Application Publication No. 2018-177654

PATENT DOCUMENT 11 Japanese Patent Application Publication No. 2009-67731

DESCRIPTION OF THE INVENTION

Solution to the Problems

However, the effect of Black ginger is not fully verified, and effects other than the above-described effects are also expected.

Therefore, concerning the above-described problems, it is an object of the present invention to provide compositions of Black ginger (*Kaempferia parviflora*) which show new effects and treatment methods utilizing these compositions.

Means for Solving the Problems

As a result of investigating the above-described problems, the inventors found that the extract of Black ginger shows an improvement in the quantity of tear fluids, treating constipation, and improving skin quality in a human study, and completed the present invention.

Namely, one aspect of the present invention is a composition and method for improving the quantity of tear fluid, which includes the extract of Black ginger (*Kaempferia parviflora*) as an active ingredient.

Another aspect of the present invention is a composition and method for treating constipation, which includes the extract of Black ginger (*Kaempferia parviflora*) as an active ingredient.

Further, another aspect of the present invention is a composition and method for improving skin quality, which includes the extract of Black ginger (*Kaempferia parviflora*) as an active ingredient.

Effects of the Invention

Therefore, the present invention can provide a composition and method for improving the quantity of tear fluid, treating constipation, and improving skin quality.

Concerning the above-described problems, it is an object of the present invention to provide compositions of Black ginger (*Kaempferia parviflora*) which show new effects and methods of using the same.

BEST MODE FOR CARRYING OUT THE PRESENT INVENTION

Hereinafter, the embodiment of the present invention is described with reference to the drawings. However, the present invention can be carried out with various embodiments and is not limited to the embodiment described below.

This embodiment of the present invention is a composition and method for improving the quantity of tear fluid, treating constipation, and improving skin quality. Specifically, it is a composition and method for improving the quantity of tear fluid, treating constipation, and improving skin quality, which contains an extract as an active ingredient from Black ginger (*Kaempferia parviflora*).

It is desirable that the part of the material of the Black ginger (*Kaempferia parviflora*) contains rhizome; however, it is not limited to it as long as it shows the above-identified effects.

It is also desirable that the place of origin of the Black ginger is a Southeast Asian Nation such as Thailand and Laos, and Okinawa of Japan, however, it is not limited to them.

Moreover, the dried or raw rhizome of Black ginger can be used as a material and subterranean parts of Black ginger can also be used.

The method of extracting the extract from Black ginger is not limited and it is possible to adopt a well-known method. It is desirable that the extractant is water, hot water, an alcohol solvent, or another organic solvent such as acetone. When the extractant is an alcohol solvent, it is desirable that it is methanol, ethanol, propanol, isopropanol, butanol, iso-butanol, and a mixture of them. When the extractant is an organic solvent, it is desirable that it is an ester such as ethyl acetate, a polyhydric alcohol such as ethylene glycol, propylene glycol or 1,3-butylene glycol, or an ether such as diethyl ether. The solvents can be used singly or combinedly. It is also desirable that the extractant is a water-containing hydrophilic solvent that contains water and a hydrophilic organic solvent. When the extractant is a water-containing hydrophilic solvent, the blend ratio of the solvent can be adjusted appropriately. Further, it is desirable that the extractant is ethanol or water-containing ethanol which contains ethanol in an amount of not less than 30 vol % and not greater than 95 vol %.

The quantity of the extractant is not limited as long as it is possible to obtain the composition that shows the above-described effect. However, it is desirable that the quantity of the extractant is not less than 2 parts by weight and not greater than 100 parts by weight when the part by weight of rhizome is assumed to be 1 part by weight.

It is also desirable that the temperature of extraction is not less than 4-degrees centigrade and not greater than 90-degrees centigrade and the time of extraction is not less than 30 minutes and not greater than 1 week.

The extraction can be performed by any arbitrary method such as stirring extraction, immersion extraction, counter-current extraction, ultrasonic extraction, or supercritical extraction.

The form of the extract of the Black ginger can be a filtrate itself which is obtained by filtering the extracted liquid, a concentrate which is obtained by concentrating the filtrate, a dry product which is obtained by drying the concentrate, a partially purified product of them, a purification product of them, or a mixture containing at least one of them.

The method of concentration can be carried out by various methods such as evaporative concentration or membrane concentration.

The method of drying can be carried out by various methods such as drying under reduced pressure, freeze-drying or spray drying.

Further, it is possible to add a diluting agent such as a dextrin if necessary.

Furthermore, the method of purification can be carried out by using one or more well-known methods to a person skilled in the art such as a synthetic adsorption resin, active carbon, ion exchange resin, Sephadex, gel filter media such as bio gel, column chromatography or recrystallization.

It is desirable that the form of the composition of the present invention is a food composition, a pharmaceutical composition or a cosmetic composition. Further, when the form is a food composition, it is desirable that the form of the composition is a functional food or health food. Furthermore, in this case, it is possible to take not only the form of a solid but also the form of a drink.

When the form of the composition is a food composition, it is also desirable that the form is a drink, a candy, a jelly, or a gummy. When the form of the composition is a health food or functional food, it is desirable that the form is a tablet, a hard capsule, a soft capsule, a powder, or a drink.

Further, when the form of the composition is a pharmaceutical composition, it is desirable that the form is suitable for oral administration such as a tablet, a capsule, a pill, a liquid, or an emulsion. Additionally, it is possible that the composition includes carriers such as an excipient, a coloring agent, a sweetness enhancing agent, and a suspending agent that are pharmaceutically allowable.

Further, when the form of the composition is a cosmetic composition, it is desirable that the form of the composition is a lotion, a cream, a pack, a gel, an emulsion, a balsam, an ointment, a liquid, a powder, or other forms which can be applied to a local part or internal part of the body.

It is also desirable that the quantity of the extraction of Black ginger of the composition is adjustable appropriately according to the prospected intake.

Further, for obtaining the effect of improving the quantity of tear fluid, constipation, or skin quality by the composition, it is desirable that the intake of the composition is not less than 10 mg and not greater than 500 mg per one day, and more desirable that it is not less than 20 mg and not greater than 300 mg per one day, further desirable that it is not less than 50 mg and not greater than 150 mg per one day.

Furthermore, the composition of Black ginger contains at least five polymethoxyflavonoids (3,5,7,3',4'-Pentamethoxyflavone, 5,7,4'-Trimethoxyflavone, 5,7-Dimethoxyflavone, 3,5,7-Trimethoxyflavone, and 3,5,7,4'-Tetramethoxyflavone). It is desirable that the total amount of the five polymethoxyflavonoids is contained in an amount not less than 4 wt %, and more desirable that it is contained in an amount not less than 10 wt % and not greater than 50 wt %. In this range, it is possible to obtain the effect of the composition.

As described above, the composition shows the effects of improving the quantity of tear fluid, constipation, and skin quantity. Further, the range of the amount of intake is the same as the above-described range, which will be clear in the below-described examples.

Therefore, according to the present invention, it is possible to provide a composition and method which has the effect of improving the quantity of tear fluid, treating constipation, and improving skin quality.

EXAMPLE

Here, the compositions described in the above-described embodiment were produced and their effect was confirmed. Hereafter, the results will be described.
(1) The Producing Method of the Composition of Black Ginger (*Kaempferia parviflora*)

The dried chip of the rhizome of Black ginger (*Kaempferia parviflora*) was pulverized by a mixer, 80 vol % ethanol was added to the pulverized material so that the amount of 80 vol % ethanol was 1 liter per 100 g of the pulverized material. After that, heating refluxing was performed for 2 hours, and the extraction (first extraction) was obtained after filtration. Further, 0.8 liters of 80% ethanol was added to the residue, heating refluxing was performed for 1 hour, and the extraction (second extraction) was obtained after filtration. Then, the first extraction and the second extraction were mixed, vacuum concentration was performed at 50 degree centigrade, an excipient was added, decompression-drying was performed at 60 degree centigrade for one evening, and 26.6 g of a solid was obtained.

By measurement using liquid chromatography of the above-described solid, it was confirmed that the extract from Black ginger contained five polymethoxyflavonoids (3,5,7,3',4'-Pentamethoxyflavone, 5,7,4'-Trimethoxyflavone, 5,7-Dimethoxyflavone, 3,5,7-Trimethoxyflavone, and 3,5,7,4'-Tetramethoxyflavone), and the total consistency of them was not less than 10 wt % and not greater than 20 wt %.
(2) Clinical Test In this test, tablets that contained 50 mg of the extract of Black ginger (*Kaempferia parviflora*) per one drop were used as test foods. On the other hand, to be the same as the appearance of the test foods, tablets that contained food coloring instead of the extract of Black ginger were used as placebo.

A random placebo-controlled double-blind study was carried out. In the study, the examinees were healthy Japanese men and women. The examinees of the intervention group took 100 mg (2 tablets per 1 day) of the extract of Black ginger (*Kaempferia parviflora*) after each breakfast with water or tepid water for 8 weeks. On the other hand, the examinees of the placebo group took placebo tablets with an equal number to the extract tablets.

Schirmer's test, in which the quantity of tear fluid is measured after 8 weeks of taking the extracts or placebos, and a questionnaire survey which relates to beauty and constipation were carried out.
(3) The Result of the Clinical Test: Schirmer's Test

TABLE 1

| Value of change between before and after taking the extract | Placebo group | Intervention group |
| --- | --- | --- |
| Right eye | −3.5 | 0.1 |
| Left eye | −2.7 | 3.4 |
| Average of right eye and left eye | −3.1 | 1.8 |

After 8 weeks of taking the test foods, in the intervention group, the length of the wet part of the test paper increased 3.4 mm at the left eye, 0.1 mm at the right eye, and 1.8 mm on average at both eyes. On the other hand, after 8 weeks of taking the placebo foods, in the placebo group, the length of the wet part of the test paper decreased 2.7 mm at the left eye, 3.5 mm at the right eye, and 3.1 mm on average at both eyes. According to the results shown in Table 1 above, it is confirmed that the extract of Black ginger is effective for improving the quantity of tear fluid and dry-eye compared with the placebo.
(4) The Result of the Clinical Test: A Questionnaire Survey The questionnaire survey was carried out according to the survey items and method for evaluation as described below.

Survey items: "I am constipated", "Wrinkles are conspicuous", "Spots are conspicuous", "Skin dullness (Yellowish, Brownish) are noticeable", and "Applying makeup is not easy".

Method for evaluation: The score was obtained by evaluating the above items by 6 steps.

1. "Never applicable", 2. "Hardly applicable", 3. "Not very applicable", 4. "A little applicable", 5. "Quite a lot applicable", 6. "Strongly applicable"

TABLE 2

| Value of score change between before and after taking the extract | Placebo group | Intervention group |
| --- | --- | --- |
| Wrinkles are conspicuous | 1.0 | −0.3 |
| Spots are conspicuous | 0.6 | −0.2 |

TABLE 2-continued

| Value of score change between before and after taking the extract | Placebo group | Intervention group |
|---|---|---|
| Skin dullness (Yellowish, Brownish) are noticeable | 1.1 | −0.3 |
| Applying makeup is not easy" | 0.8 | −0.3 |

TABLE 3

| Value of score after taking the extract | Placebo group | Intervention group |
|---|---|---|
| I am constipated | 2.6 | 1.6 |

According to the above-described Table 2 and Table 3, compared with the placebo group, it was confirmed that the skin quality and constipation were improved by taking the extract of Black ginger.

Therefore, by the above-described human study, it was confirmed that the composition and method of the present invention had effects for improving the quantity of tear fluid, treating constipation, and improving skin quality.

What is claimed is:

1. A method of treating a human in need of an increased quantity of tear fluid in their eye, the method consisting essentially of administering to the human in need thereof a therapeutically effective amount of an extract of the rhizome of Kaempferia parviflora to effectively treat the human in need of an increased quantity of tear fluid in their eye, wherein the extract consists essentially of 3,5,7,3',4'-Pentamethoxyflavone, 5,7,4'-Trimethoxyflavone, 5,7-Dimethoxyflavone, 3,5, 7-Trimethoxyflavone, and 3,5,7,4'-trimethoxyflavone, and the total mass of them in the entire method is not less than 10 wt. % and not greater than 20 wt. %.

* * * * *